United States Patent
Richman

[11] 3,987,128
[45] Oct. 19, 1976

[54] TETRACYCLIC TETRAAMINO PHOSPHORANES AND METHOD OF PREPARATION

[75] Inventor: Jack Eugene Richman, Wilmington, Del.

[73] Assignee: E. I. Du Pont de Nemours and Company, Wilmington, Del.

[22] Filed: Aug. 22, 1975

[21] Appl. No.: 606,779

[52] U.S. Cl. ............................. 260/936; 106/15 FP; 260/239 EP; 260/239 BC; 260/239 A; 260/239 B; 260/293.60; 260/326.61; 260/543 F; 260/543 PN; 260/551 P
[51] Int. Cl.² ...................... C07F 9/09; C07F 9/22; C07F 9/26; C07F 9/58
[58] Field of Search....... 260/551 P, 239 BC, 543 F, 260/543 PN, 936, 239 EP, 239 A, 239 B, 293.60, 326.61

[56] References Cited
OTHER PUBLICATIONS
Demitres et al., CA 62:428e (1965).
Czieslik et al., CA 78:111407t (1973).

Primary Examiner—Robert V. Hines
Assistant Examiner—Thomas A. Waltz

[57] ABSTRACT

Tetracyclic tetraamino phosphoranes of the formula

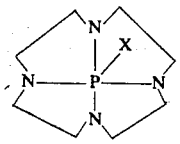

wherein X is F, $C_6H_5$, or $C_1$–$C_6$ alkyl, and tricyclic polyamino phosphine oxides of the formula

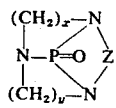

wherein x and y are each 2 or 3
Z is $-(CH_2)_{\overline{z}}-$ where z is 2 to 10 and $x + y + z$ is 7 to 14 or
Z is $-(CH_2)_{\overline{v}}-NH-(CH_2)_{\overline{w}}-$ where v and w are each 2 or 3
are prepared by reacting a silylated cyclic polyamine of the formula

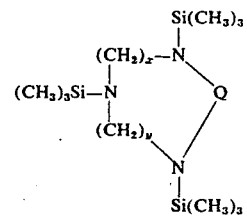

wherein
Q is $-(CH_2)_{\overline{z}}-$ or

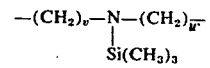

with a fluorophosphorane of the formula $$XPF_4$$

or $$POF_3,$$

provided that when Q is $-(CH_2)_{\overline{z}}-$, the fluorophosphorane is $POF_3$. The corresponding alkoxy or amino [X=OR, $NR_2$ or $N(CH_2)_{2-6}$, where R is $C_1$–$C_6$ alkyl] tetracyclic tetraaminophosphoranes are obtained by reaction of an alkali metal alkoxide or amide with the tetracyclic fluorophosphorane. The methyl iodide salts of the tetracyclic tetraamino phosphoranes are also described. All of the polycyclic polyamino phosphoranes and phosphine oxides are useful as flame retardants for cotton.

9 Claims, No Drawings

TETRACYCLIC TETRAAMINO PHOSPHORANES AND METHOD OF PREPARATION

BACKGROUND OF THE INVENTION

1. Field of the Invention

This invention relates to polycyclic polyamino phosphoric compounds and more particularly to tetracyclic tetraamino phosphoranes and tricyclic polyamino phosphine oxides, methods of their preparation, and their use as flame retardants for cotton.

2. Description of the Prior Art

The preparation of dialkylaminophosphoranes is known. In *Z. Chem.*, 8, 246–247(1968) M. Murray and R. Schmutzler describe the reaction of silylated amines with $PF_5$ to give mono-and bis(dialkylamino)phosphoranes, and an alternate syntheses of tris(dialkylamino)-difluorophosphoranes.

In *Compt. Rend.*, Series C, 274, 2209 (1972) Y. Charbonnel and J. Barrons describe a spirophosphorane of the formula.

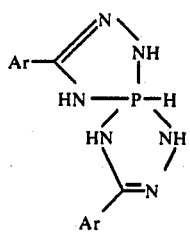

SUMMARY OF THE INVENTION

This invention is based on the discovery of tetracyclic tetraamino phosphoranes of the formula

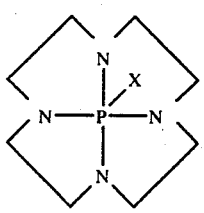

wherein X is F, $C_6H_5$, R, OR, $NR_2$ or $N(CH_2)_{2-6}$, where R is $C_1$–$C_6$ alkyl, and monomethyl iodide salts thereof. It also relates to the discovery of tricyclic polyamino phosphine oxides of the formula

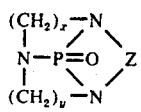

wherein $x$ and $y$ are 2 or 3, and

Z is $-(CH_2)_z-$ where $z$ is 2 to 10 and $x + y + z$ is 7 to 14, or

Z is $-(CH_2)_v-NH-(CH_2)_w-$ where $v$ and $w$ are each 2 or 3.

These polycyclic polyamino phosphoric compounds are prepared by reacting a silylated cyclic polyamine of the formula

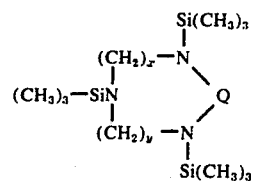

wherein
Q is $-(CH_2)_z-$ or

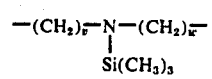

with a fluorophosphorane selected from the group consisting of $$XPF_4 \text{ and } POF_3$$

wherein X is F, $C_6H_5$, or $C_1$–$C_6$ alkyl at a temperature from room temperature to about 200° C, provided that when Q is $-(CH_2)_z-$, the fluorophosphorane is $POF_3$. The alkoxy and amino [X=OR, $NR_2$ or $N(CH_2)_{2-6}$] tetracyclic tetraaminophosphoranes are prepared by reacting an alkali metal alkoxide or amide with the corresponding fluorophoshorane.

DETAILED DESCRIPTION OF THE INVENTION

The tetracyclic tetraamino phosphoric compounds of this invention are prepared by reacting a silylated cyclic tetraamine with a fluorophoshorane in accordance with the equation

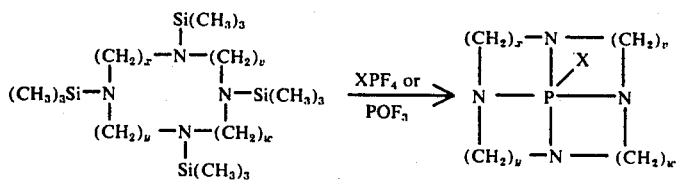

at a temperature from about room temperature to about 200° C.

Phosphorus pentafluoride ($PF_5$) and phosphorus oxyfluoride ($POF_3$) are commercially available products. Fluorophosphoranes of the formula $XPF_4$ where X is $C_6H_5$, or $C_1$–$C_6$ alkyl are prepared by the method described by Schmutzler in *Inorg. Chem.*, 3, 410–415 (1964).

The silylated cyclic tetraamines are prepared by reacting the corresponding cyclic tetraamine with a strong base such as sodium hydride, or an organo lithium reagent, for example, methyl lithium, butyl lithium or phenyl lithium and then with trimethylchlorosilane $ClSi(CH_3)_3$ in accordance with the equations

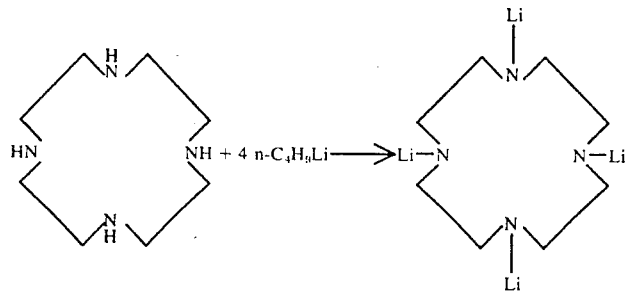

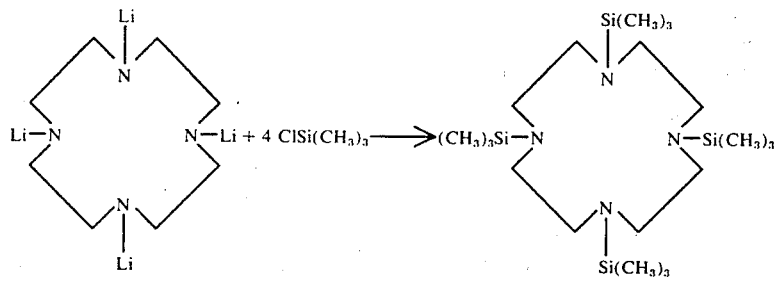

Trimethylchlorosilane is a commercially available product. Suitable cyclic tetraamines for use in this process include 1,4,6,11-tetraazacyclododecane; 1,4,7,10-tetraazacyclotridecane; 1,4,7,11-tetraazacyclotetradecane; 1,4,8,11-tetraazacyclotetradecane; 1,4,8,12-tetraazacyclopentadecane; 1,5,9,13-tetraazacyclohexadecane; and the like.

These cyclic tetraamines are prepared by the method outlined by Richman and Atkins in J. Amer. Chem. Soc., 96, 2268 (1974). Using this method the tetrahydrochloride salt of the cyclic tetraamine is prepared, the salt is treated with aqueous caustic solution to form the free base, and the free base is isolated from the aqueous base by extraction with benzene, concentrated and finally sublimed under vacuum.

The tetracyclic tetraamino phosphoranes of this invention in which X is $C_6H_5$, R, or $NR_2$ or $N(CH_2)_{2-6}$ can also be prepared by reacting the 13-fluoro tetracyclic phosphorane with an alkali metal compound of the formula MX where M is alkali metal in accordance with the equation

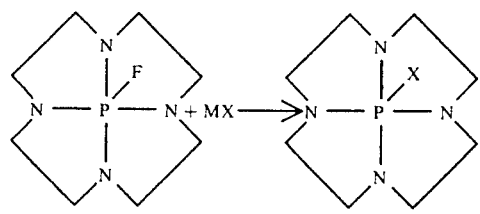

Suitable alkali metal compounds include sodium methoxide, n-butyllithium phenyllithium and the lithium salts of methanol, propanol, pentanol, hexanol, dimethylamine, dihexylamine, ethyleneimine, pipridine, hexamethyleneimine, and the like.

The monomethyl iodide salts of the tetracyclic phosphoranes are prepared by reacting the tetracyclic phosphorane with methyl iodide in accordance with the equation

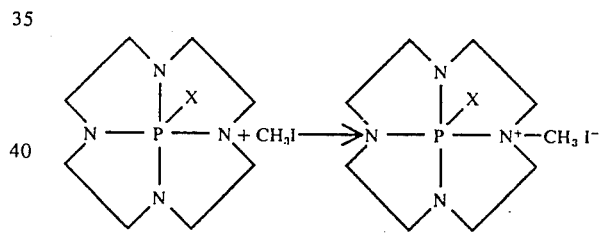

The tricyclic tetraamino phosphine oxides of this invention are prepared by hydrolyzing a tetracyclic tetraamino phosphorane in accordance with the equation

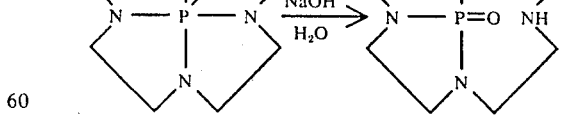

These tricyclic tetraamino phosphine oxides can also be prepared in one step without isolating the intermediate tetracyclic tetraamino phosphorane by reacting the silylated cyclic tetraamine with phosphorus pentafluoride in accordance with the equation

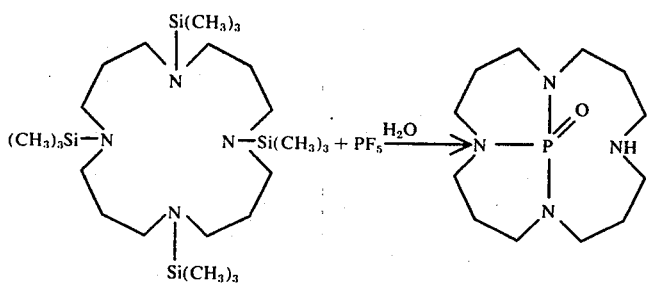

This procedure allows the preparation of tricyclic tetraamino phosphine oxides where the intermediate tetracyclic tetraamino phosphorane is not structurally stable.

The tricyclic triamino phosphine oxides of this invention are prepared by reacting a silylated cyclic triamine with phosphorus oxyfluoride in accordance with the equation

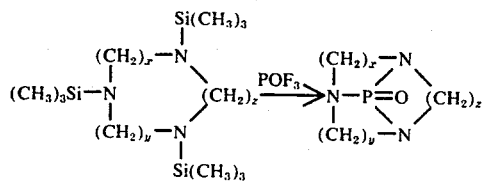

at a temperature from room temperature to about 200° C.

The silylated cyclic triamines are prepared by reacting the corresponding cyclic triamine with a strong base and reacting this product with trimethylchlorosilane in the same manner as silylated cyclic tetraamines are prepared from cyclic tetraamines. Suitable cyclic triamines include 1,4,7-triazacyclodecane; 1,4,8-triazacycloundecane; 1,5,9-triazacyclododecane and 1,4,7-triazacyclododecane.

The polycyclic polyamino phoshoric compounds of this invention and the monomethyl iodide salts are crystalline solids or distillable liquids. These materials are useful as flame retardants for cotton. The phosphoric compound is dissolved in a suitable solvent such as dimethylformamide and the cotton is treated with the solution.

EXAMPLES OF THE INVENTION

The following examples illustrate the novel tetracyclic tetraamino phosphoranes and tricyclic polyamino phosphine oxides of this invention, their preparation, and their use as flame retardants. All percentages are by weight, and all temperatures are in degrees Centigrade.

EXAMPLE 1 (E5985-19,38,43,59 & 60)

A. 1,4,7,10-Tetrakis(trimethylsilyl)-1,4,7,10-tctraazacyclododecane was prepared as follows

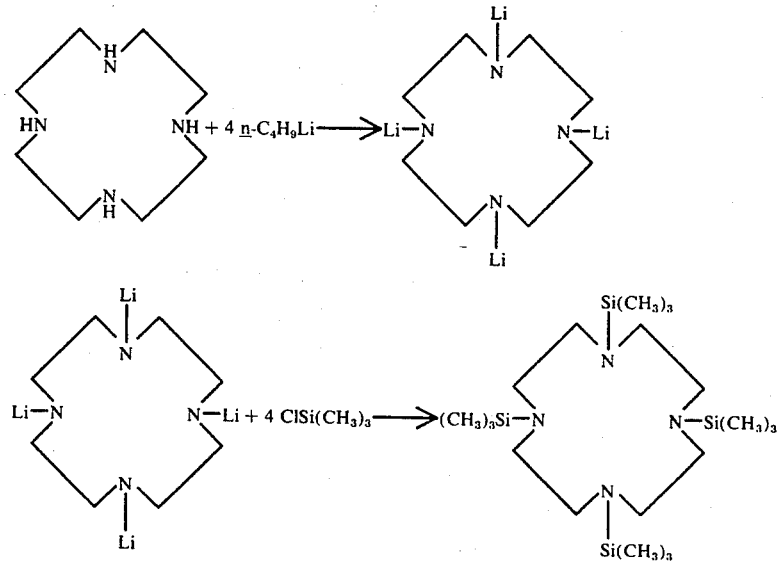

A slurry of 0.69 g of 1,4,7,10-tetraazacyclododecane in 20 ml of anhydrous tetrahydrofuran was cooled in a Dry Ice/acetone bath and stirred under nitrogen as 10 ml of a 1.6M n-butyllithium/hexane solution was quickly added. The milky slurry was stirred for 15 min at −78°, and then was warmed and stirred at 0° for 30 min. The mixture was again cooled in a Dry Ice/acetone bath and 2.1 ml of trimethylchlorosilane was added. This mixture was stirred at room temperature overnight, and then filtered under nitrogen and concentrated to 2.3 g of white solid while avoiding undue exposure to air. This solid was slurried in petroleum ether, filtered, and vacuum dried. The analytical sample was sublimed at 110°/0.1 mm giving a white solid melting at 140°–150°.

Anal. Calcd. for C$_{20}$H$_{52}$N$_4$Si$_4$: C, 52.11; H, 11.37; N, 12.15
Found: C, 51.78; H, 11.32; N, 12.28
51.86  11.20  12.34

NMR(CDCl$_3$): δ 2.82 (s, CH$_2$, 16H) and 0.0 (s, CH$_3$, 33–36H).

The infrared spectrum was taken on a sample similarly prepared on a ten fold scale.

IR(KBr): 3.38, 6.82(w), 7.50, 7.85, 8.03, 8.57(w), 9.16, 9.28, 9.92, 10.2, 11.7(b), 12.02(st), and 13.3μ.

B. 13-Fluoro-1,4,7,10-tetraaza-13-phosphatetracyclo[5.5.1.0$^{4,13}$.0$^{10,13}$]tridecane was prepared as follows

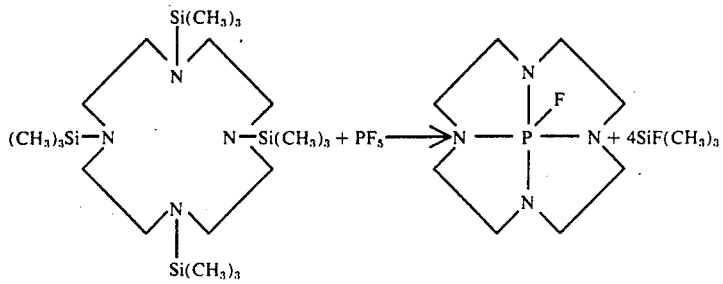

A solution of 1.0 g of 1,4,7,10-tetrakis(trimethylsilyl)-1,4,7,10-tetraazacyclododecane (sublimed) in 10 ml of o-dichlorobenzene was frozen and evacuated. This mixture was melted and stirred at 25° as 50 ml of phosphorus pentafluoride gas was added. Then nitrogen gas was added to atmospheric pressure. After 30 min the soluton was heated at 100° for 1 hr, then at 145° for 4 hr. The solvent was removed under vacuum and the residue distilled at 110° and 0.1 mm pressure thereby giving clear colorless crystals of 13-fluoro-1,4,7,10-tetraaza-13-phosphatetracyclo[5.5.1.0$^{4,13}$.0$^{10,13}$]tridecane, mp 87–95°. This sample was used for ir, nmr and mass spectroscopy. A benzene solution of this solid, which was used for $^{31}$P nmr, was concentrated and sublimed at 90° and 0.1 mm pressure for the X-ray crystal structure sample.

IR(KBr): 3.42, 3.53, 6.80, 7.25, 7.46, 8.0, 8.14, 8.35, 8.86, 9.21, 10.16, 10.23, 11.5, 12.67, 13.4 and 14.0μ.

NMR(CDCl$_3$, 60 MHz): Asymmetric 29 line pattern, 2.7–3.3 ppm.

NMR(CDCl$_3$, $^{19}$F, 94.1 MHz): -75.4 ppm (doublet, J$_{PF}$ = 793.5 Hz).

NMR(C$_6$H$_6$, $^{31}$P, 36.43 MHz): -14.19 ppm (doublet, J$_{PF}$ = 799 Hz).

The mass spectrum shows the parent ion at m/e 218 with prominent fragment ions at m/e 217, 176, 135, 78, 56, and 42.

X-ray cyrstal structure determination confirmed the structure.

EXAMPLE 2 (E8186-26,28,40)

13-Fluoro-1,4,7,10-tetraaza-13-phosphatetracyclo[5.5.1.0$^{4,13}$.0$^{10,13}$]tridecane was prepared as follows

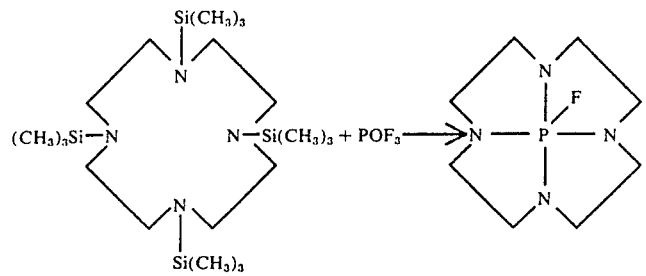

A mixture of 400 mg of 1,4,7,10-tetrakis(trimethylsilyl)-1,4,7,10-tetraazacyclododecane and 2.0 ml chlorobenzene was frozen and evacuated in a 50 ml flask, and then 20–21 ml of phosphorus oxyfluoride gas was added. The flask was sealed and warmed for 5 min at 100°, cooled, pressured to one atmosphere with nitrogen, and then stirred at 60° for 2 hr. A sample of this mixture suggested no reaction. The mixture was frozen and evacuated, and 25 ml of phosphorus oxyfluoride was added. This sealed flask was heated at 100° for 17 hr. After standing for 1–2 days the reaction mixture was filtered and concentrated under nitrogen. The residue was distilled bulb-to-bulb at 115° and 0.1 mm pressure to give 70–80 mg of a semi-solid distillate. Distillation was continued at 160–190° oven temperature giving 30 mg of sublimate, mp 98°–100°. This sample was identified by nmr and mass spectroscopy as 13-fluoro-1,4,7,10-tetraaza-13-phosphatetracyclo[5.5.1.0$^{4,13}$.0$^{10,13}$]tridecane. The mass spectrum shows the predominant characteristic ions of this prodút at m/e 218 (parent) and m/e 217 (most abundant ion), and no significant ions at higher values of m/e.

EXAMPLE 3 (E8186-25,27,41)

13-Methyl-1,4,7,10-tetraaza-13-phosphatetracyclo[5.5.1.0$^{4,13}$.0$^{10,13}$]tridecane was also prepared as follows

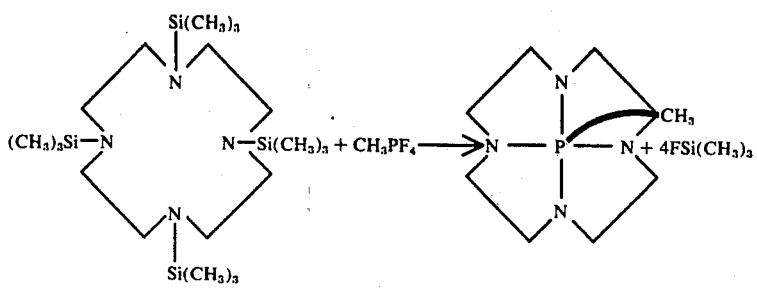

A suspension of 0.40 g of 1,4,7,10-tetrakis(trimethylsilyl)-1,4,7,10-tetraazacyclododecane in 2 ml of chlorobenzene was stirred as 25 ml of methyltetrafluorophosphane gas was bubbled into the mixture. This mixture was stirred at 90°–105° for 2 hr, cooled to 25°, and then heated at 120°–125° for 2 hr. A sample was filtered under nitrogen into an nmr tube. The nmr spectrum indicated that approximately 30% of the silyl groups had been displaced at this point. The sample was sealed under vacuum and heated in an oven at 150° for a total of 39.5 hr. The nmr of this sample indicated a 75–77% yield of 13-methyl-1,4,7,10-tetraaza-13-phosphatricyclo[5.5.1.0$^{4,13}$.0$^{10,13}$]tridecane.

The product was isolated from a scaled-up procedure similar to the above procedure for the nmr sample except that a head of 230 mm of Hg was used to raise the temperature of the refluxing solution to 142°–143° instead of sealing in a closed system. Refluxing for 7 hr was followed by concentrating the mixture to 2 g and finally distilling bulb-to-bulb at an oven temperature of 120°–140° and 1.0 mm pressure to give 0.77 g (82% yield) of clear light yellow 13-methyl-1,4,7,10-tetraaza-13-phosphatetracyclo[5.5.1.0$^{4,13}$.0$^{10,13}$]tridecane distillate. This sample gave the following nmr.

NMR(CDCl$_3$): δ 1.25 (doublet, $J_{PH}$ = 13.9 Hz, 2.9H) and 2.86 (center of 18 line nearly symmetric multiplet, 16H).

This spectrum shows virtual identity to that of 13-methyl-1,4,7,10-tetraaza-13-phosphatetracyclo[5.5.1.0$^{4,13}$.0$^{10,13}$]tridecane prepared by methylation of 1,4,7,10-tetraaza-13-phosphatetracyclo[5.5.1.0$^{4,13}$.0$^{10,13}$]tridecane with the addition of a single additional line in the methylene multiplet (minor impurity). This alternate sample was characterized by ir, mass spectra and elemental analysis.

IR(CHCl$_3$): 3.44, 3.53, 6.78, 7.38, 7.48, 7.73, 8.00, 8.14, 8.39, 8.95, 9.26, 11.3, and 11.52μ.

The mass spectrum shows the parent ion at m/e 214 and major fragment ions at m/e 213, 200, 199, 197, 142, 101, 74, 58, 56, 42, 28, and 18.

| Anal. Calcd. for C$_9$H$_{19}$N$_4$P: | C, 50.45; | H, 8.94; | N, 26.15; |
|---|---|---|---|
| | P, 14.46. | | |
| Found: | C, 50.54; | H, 8.81; | N, 26.13; |
| | 50.79 | 8.64 | 26.13 |
| | P, 14.58. | | |

EXAMPLE 4 (E5985-23,26,27,29)

13-Phenyl-1,4,7,10-tetraaza-13-phosphatetracyclo[5.5.1.0$^{4,13}$.0$^{10,13}$]tridecane was prepared as follows

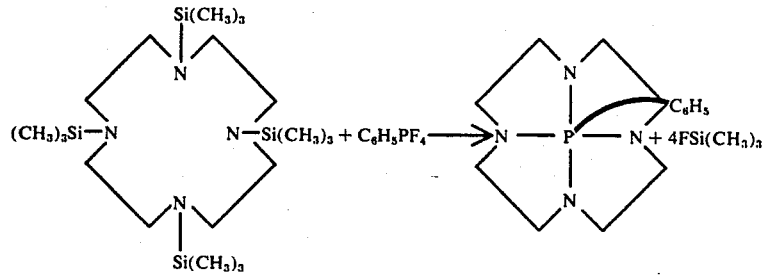

A. A mixture of 2.80 g of 1,4,7,10-tetrakis(trimethylsilyl)-1,4,7,10-tetraazacyclododecane (sublimed), 1.35 g of freshly distilled phenyltetrafluorophosphorane (bp 130°–135°) and 25 ml of Freon 112 (bp 92.8°) was stirred at room temperature and a sample (about 0.5 ml) removed for nmr. After standing overnight the nmr spectrum indicated that one-fourth of the silyl groups were displaced as trimethylfluorosilane. The nmr sample was concentrated and then dissolved in o-dichlorobenzene. The sample was heated under nitrogen at 150°–155° for 3 hr, concentrated and dissolved in deuterochloroform for nmr. The nmr spectrum indicated that the reaction was now complete and that all the silyl groups has been displaced. The remaining sample was then reconcentrated, and the residue recrystallized from cyclohexane giving white prisms of 13-phenyl-1,4,7,10-tetraaza-13-phosphatetracyclo[5.5.1.0$^{4,13}$.0$^{10,13}$]tridecane, mp 140°–143°.

The main batch of the original Freon 112 reaction mixture after refluxing 1.5 hr was shown to have proceeded to displacement of one-fourth of the silyl groups. This mixture was concentrated under vacuum, dissolved in 30 ml of o-dichlorobenzene, and heated in an oil bath at 150°–160° for 1.5 hr. This mixture was distilled to near dryness and then cooled and evacuated leaving a thick semi-solid. This material was triturated with 30 ml of boiling cyclohexane and the cyclohexane solution concentrated to 10 ml. Crystals of 13-phenyl-1,4,7,10-tetraaza-13-phosphatetracyclo[5.5.1.0$^{4,13}$.0$^{10,13}$]tridecane grew at 5°. This sample was sublimed at 85° and 0.1 mm pressure to obtain the analytical sample, mp 139°–142°.

| Anal. Calcd. for C$_{14}$H$_{21}$N$_4$P: | C, 60.85; P, 11.21. | H, 7.66; | N, 20.28; |
|---|---|---|---|
| Found: | C, 61.13; P, 11.21 11.51 | H, 7.57; | N, 20.43; |

The mass spectrum of this compound shows the parent ion at m/e 276 with major fragments at m/e 275, 274, 199, 197, 109, 56, and 42.

The infrared spectrum was taken on a sample similarly prepared.

IR(KBr): 3.25, 3.43, 3.56, 6.80, 6.95, 7.29, 7.49, 8.00, 8.15(st), 8.23, 8.38(st), 8.98(st), 9.13, 9.25, 9.40, 9.72(w), 11.56, 11.84, 13.11, 13.48(st) and 14.3 μ.

NMR(CDCl$_3$): δ 2.90 (doublet, $J_{PH}$ (?) = 10.8 Hz, 16H) and 7.16–7.85 (m, 5H).

B. A similar reaction run on 5.0 g of 1,4,7,10-tetrakis(trimethylsilyl)-1,4,7,10-tetraazacyclododecane in o-dichlorobenzene gave a 90% yield of 13-phenyl-1,4,7,10-tetraaza-13-phosphatetracyclo[5.5.1.0$^{4,13}$.0$^{10,13}$]tridecane, mp 140°–142°.

ml of anhydrous tetrahydrofuran under nitrogen was cooled in a Dry Ice/acetone bath and treated with 1.6 ml of 1.6M n-butyllithium in hexane (Foote Mineral Company). After 15 min at −78°, the mixture was stirred for 30 min at 0° and then for 2.5 days at 25°. It was refluxed for 30 min, cooled, filtered under nitrogen, and concentrated. The residue was slurried in warm hexane, filtered and concentrated again leaving a clear colorless oil. This oil was distilled bulb-to-bulb at 90°–100° oven temperature and 0.2 mm pressure giving 0.36 g of clear fluid which was identified as the n-butylphoshorane by ir, nmr and mass spectroscopy, and by elemental analyses.

NMR(CDCl$_3$, 220 MHz): δ 2.7–3.1 (26 line nearly symmetrical multiplet centered at 2.89 ppm, 16H), 1.65 (broadened m, P-CH$_2$), 1.45 (broadened m, P-CH$_2$CH$_2$), 1.30 (six line, CH$_2$CH$_3$), and 0.89 (t, J∼7 Hz, CH$_3$).

IR(neat): 3.40, 3.46, 3.54, 6.82, 7.31, 7.51, 8.03, 8.2(doublet), 8.40(st), 8.70, 8.96(st), 9.25, 9.40, 10.17, 10.2–10.4, 11.56, 12.7, 13.0, 13.6, and 13.8μ.

The mass spectrum shows the parent ion at m/e 256 and major fragments at m/e 200, 199, 144, 101, 74, 60, 59, 58, 56, 42.

| Anal. Calcd. for C$_{12}$H$_{25}$N$_4$P: | C, 56.23; P, 12.08. | H, 9.83; | N, 21.86; |
|---|---|---|---|
| Found: | C, 54.55, 54.95 P, 12.05. | H, 9.81; 9.85 | N, 22.68; 22.58 |

EXAMPLE 5 (E5985-100)

13-n-Butyl-1,4,7,10-tetraaza-13-phosphatetracyclo[5.5.1.0$^{4,13}$.0$^{10,13}$]tridecane was prepared as follows

EXAMPLE 6 (E8186-63)

13-(1-Pyrrolidyl)-1,4,7,10-tetraaza-13-phosphatetracyclo[5.5.1.0$^{4,13}$.0$^{10,13}$]tridecane was prepared as follows

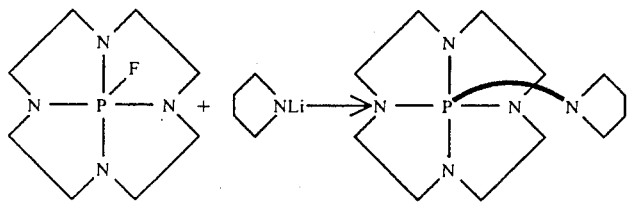

A solution of 0.15 g of dry pyrrolidine in 1 ml of n-hexane was treated with 0.6 ml of 1.6M n-butyllithium in hexane under a nitrogen atmosphere. After 10 min 1 ml of dry tetrahydrofuran was added. Then 0.20 g of 13-fluoro-1,4,7,10-tetraaza-13-phosphatetracyclo[5.5.1.0$^{4,13}$.0$^{10,13}$]tridecane was added as a solid. The resulting solution was diluted with 1 ml of tetrahydrofuran and refluxed for 2 hr. After standing overnight, 1.0 ml of pyrrolidine was added and the mixture was refluxed for 7 hr. The resulting slurry was concentrated and distilled bulb-to-blub at 65°–96°/0.1 mm giving 0.20 g of crystalline solid identified by ir, nmr,

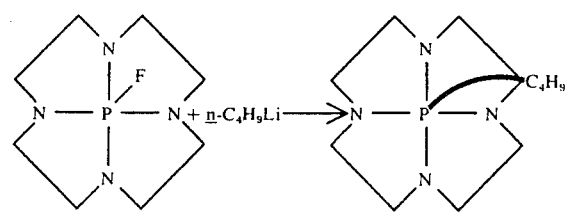

A solution of 0.55 g of 13-fluoro-1,4,7,10-tetraaza-13-phosphatetracyclo]5.5.1.0$^{4,13}$.0$^{10,13}$]tridecane in 20 and mass spectroscopies as a mixture containing 80–90% of 13-(1-pyrrolidyl)-1,4,7,10-tetraaza-13-phosphatetracyclo[5.5.1.0$^{4,13}$.0$^{10,13}$]tridecane and 10–20% of the initial fluorophosphorane. These estimates were made by comparing the spectroscopic data with that of pure samples of the two compounds.

The new compound was also prepared by the reaction of 1,4-7,10-tetraaza-13-phosphatetracyclo-[5.5.1.0$^{4,13}$.0$^{10,13}$]tridecane with t-butylhypochlorite and pyrrolidine. The data below are for the pure compound, mp 86°–88°.

| Anal. Calcd. for C$_{12}$H$_{24}$N$_5$P: | C, 53.51; | H, 8.98; | N, 26.01; |
|---|---|---|---|
| | P, 11.50 | | |
| Found: | C, 54.07; | H, 8.99; | N, 26.23; |
| | P, 12.63 | | |

NMR(CDCl$_3$, 220 MHz): 1.64 (m, 4H), 3.21 (m, 4H), and 2.87 (approximate center of an asymmetric 26 line multiplet, 16H).

IR(KBr): 3.36, 3.48, 3.55, 6.81, 7.28, 7.48, 8.03, 8.17 (st), 8.36 (st), 8.94 (st), 9.27, 9.43, 9.98, 10.21, 10.36, 10.9 (w), 11.6, 13.23 and 14.20 $\mu$.

The mass spectrum has the parent ion at m/e 269 with major fragments at m/e 201, 200, 199 and 101.

EXAMPLE 7 (E5985-67)

13-Methoxy-1,4,7,10-tetraaza-13-phosphatetracyclo[5.5.1.0$^{4,13}$.0$^{10,13}$]tridecane was prepared as follows

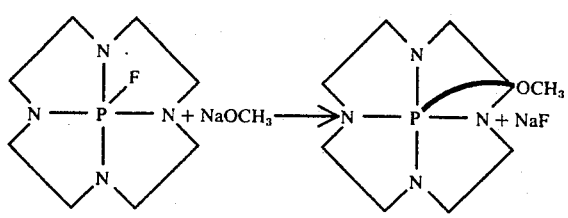

A. Five ml of 1 molal sodium methoxide/methanol and 0.54 g of 13-fluoro-1,4,7,10-tetraaza-13-phosphatetracyclo[5.5.1.0$^{4,13}$.0$^{10,13}$]tridecane was stirred for approximately 30 min at 25°. This mixture was concentrated and distilled bulb-to-bulb at 85° and 0.1 mm pressure. The nmr spectrum of the distillate suggests mainly starting phosphorane with 20–40% of 13-methoxy tetracyclic phosphorane which shows in the nmr spectrum a doublet at the expected position for the methoxy group ($\delta$ 3.50, $J_{PH}$ = 12.4 Hz).

B. This experiment was repeated with refluxing of the reaction mixture for 30 min and similar work-up. The nmr of this product shows an 82.18 ratio of 13-methoxy:13-fluoro based on relative integration of the methyl and methylene regions.

NMR(CDCl$_3$): $\delta$ 3.51 (doublet, $J_{PH}$ = 12.4 Hz, CH$_3$) and 2.6–3.2 (nearly symmetrical multiplet).

The mass spectrum shows the parent ion of the 13-methoxy tetracyclic phosphorane at m/e 230 and the parent ion of the 13-fluoro tetracyclic phosphorane at m/e 218. After adjusting for the ions characteristic of the 13-fluorotetracyclic phosphorane other major fragment ions for the 13-methoxy tetracyclic phosphorane were m/e 229, 216, 199, 78, 56, 42, 41, 32, 31, 30, 29, 28, 27 and 18.

The infrared spectrum (CHCl$_3$) shows a great similarity to that of the 13-fluoro tetracyclic phosphorane with additional bands at 5.94, 7.99, 14.27 and especially 9.53$\mu$.

EXAMPLE 8 (E5985-150,155)

The monomethyl iodide salt of 13-fluoro-1,4,7,10-tetraaza-13-phosphatetracyclo[5.5.1.0$^{4,13}$.0$^{10,13}$]tridecane was prepared as follows

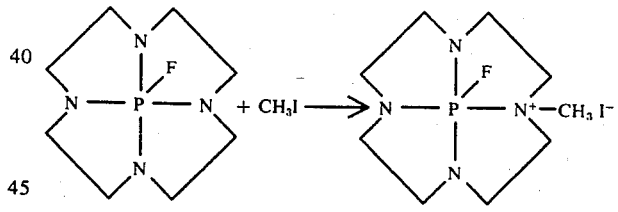

A solution of 0.050 g of 13-fluoro-1,4,7,10-tetraaza-13-phosphatetracyclo[5.5.1.0$^{4,13}$.0$^{10,13}$]tridecane in 0.5 ml of acetonitrile-d$_3$ was treated with 0.041 g of methyl iodide. Clear prisms weighing 62 mg separated. These crystals were identified by nmr as the monomethyl iodide salt of 13-fluoro-1,4,7,10-tetraaza-13-phosphatetracyclo[5.5.1.0$^{4,13}$.0$^{10,13}$]tridecane. This data is consistent with the above structure.

NMR(CD$_3$CD, 220 MHz): $\delta$ 3.56 (sextuplet, J ~ 5.7 Hz, 2H) 3.46–3.04 (complex multiplet), and 2.85 (doublet of doublets, $J_{PH}$ = 4.3 Hz, $J_{FH}$ = 3.2 Hz, CH$_3$). Phosphorus and fluorine couplings were verified by $^{31}$P and $^{19}$F decoupling experiments at 100 MHz.

NMR($^{19}$F, CD$_3$OD): doublet at −80.88 ppm ($J_{PF}$ = 928.5 Hz).

Another sample prepared by essentially the same procedure was used for the analytical sample, mp 262°–273°.

| Anal. Calcd. for $C_9H_{19}N_4PFI$: | C, 30.01; | H, 5.32; | N, 15.56; |
| --- | --- | --- | --- |
|  | F, 5.28. |  |  |
| Found: | C, 29.98; | H, 5.27; | N, 15.73; |
|  | F, 5.34. |  |  |

EXAMPLE 9 (E5985-151)

The monomethyl iodide salt of 13-methyl-1,4,7,10-tetraaza-13-phosphatetracyclo[5.5.1.0$^{4,13}$.0$^{10,13}$]tridecane was prepared as follows

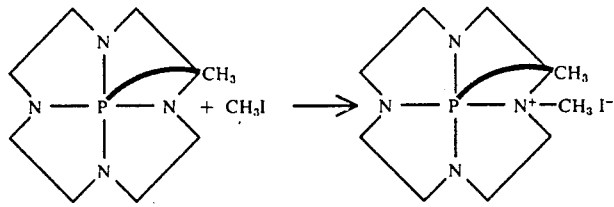

By a procedure similar to Example 8, methylation of 13-methyl-1,4,7,10-tetraaza-13-phosphatetracyclo[5.5.1.0$^{4,13}$.0$^{10,13}$]tridecane gave cyrstals, mp 260°–270° (dec), identified by nmr as the monomethyl iodide salt of 13-methyl-1,4,7,10-tetraaza-13-phosphatetracyclo[5.5.1.0$^{4,13}$.0$^{10,13}$]tridecane. This data is consistent with the above structure.

NMR(CD$_3$OD): δ 2.8–3.5 (complex multiplet), 2.77 (doublet, J$_{PH}$≈1.5 Hz, N-CH$_3$), and 1.97 (doublet, J$_{PH}$≈15.5 Hz, PCH$_3$).

EXAMPLE 10 (E5985-148,149)

The monomethyl iodide salt of 13-phenyl-1,4,7,10-tetraaza-13-phosphatetracyclo[5.5.1.0$^{4,13}$.0$^{10,13}$]tridecane was prepared as follows

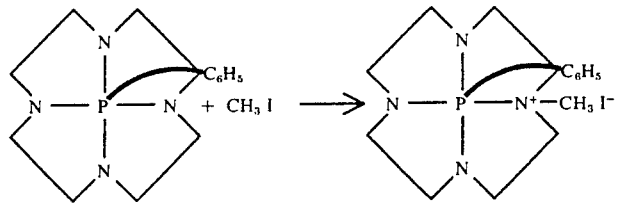

A mixture of 100 mg of 13-phenyl-1,4,7,10-tetraaza-13-phosphatetracyclo[5.5.1.0$^{4,13}$.0$^{10,13}$]tridecane and 1 ml of methyl iodide was stirred for 5 min and then 3 ml of methanol was added. After 1 hr at 25°, the solution was concentrated and dissolved in isopropanol (5 ml). This solution was filtered and seeded with crystals obtained by scratching a small sample. The resulting white crystals (mp 167°–168°) weighing 65–70 mg were collected. This sample was identified by nmr and ir as the monomethyl iodide salt of 13-phenyl-1,4,7,10-tetraaza-13-phosphatetracyclo-[5.5.1.0$^{4,13}$.0$^{10,13}$]tridecane.

NMR(CD$_3$OD, 220 MHz): δ 7.69 (doublet of multiplets, J$_{PH}$≈17 Hz, ortho, 2H), δ 7.56 (multiplet, 3H), δ 3.21–3.63 (3 sets of multiplets in the ratio 2:6:2H), 3.14–2.82 (2 sets of multiplets in the ratio 4:2H) and 1.78 (doublet, J$_{PH}$ = 2.5 Hz, 3H).

IR(KBr): 2920, 2860, 1591, 1468, 1461, 1452, 1438, 1346, 1280, 1262, 1232, 1191, 1165, 1142, 1130, 1088, 1080, 1056, 1034, 1010, 981, 969, 959, 934, 881, 779, 749, 711, 673, 641, 628, 530, 515, 436, and 355 cm$^{-1}$.

A similar experiment, but using isopropanol solvent and only a 20% excess of methyl iodide, gave cyrstals which were used for elemental analysis.

| Anal. Calcd. for $C_{15}H_{24}N_4PI$: | C, 43.07; | H, 5.78; | N, 13.40; |
| --- | --- | --- | --- |
|  | I, 30.34. |  |  |
| Found: | C, 42.88; | H, 5.74; | N, 13.46; |
|  | I, 28.56. |  |  |

EXAMPLE 11 (E5985-65)

13-Oxo-1,4,7,10-tetraaza-13-phosphatricyclo[5.5.1.0$^{4,13}$]tridecane was prepared as follows

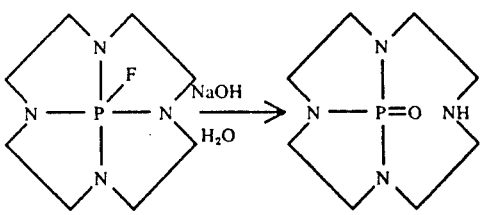

A 100 mg sample of 13-fluoro-1,4,7,10-tetraaza-13-phosphatetracyclo[5.5.1.0$^{4,13}$.0$^{10,13}$]tridecane was dissolved in 0.5 ml of 1N sodium hydroxide by heating to near boiling. This mixture was cooled, filtered and evaporated. The white residue was then sublimed at 150°–180° and 0.1 mm pressure to give 90 mg of 13-oxo-1,4,7,10-tetraaza-13-phosphatricyclo[5.5.1.0$^{4,13}$]-tridecane and leaving 10–20 mg of residue. The sublimate was kept under dry nitrogen and melted at 215°–217° to a clear colorless melt. On exposure to moist air this solid picked up water of hydration without softening. The hydrated sample softened at 90° and slowly lost water up to 160° where the sample frothed and then darkened and totally melted in the range of 200°–210°. The anhydrous sample was used for nmr and mass spectra.

NMR(CDCl$_3$): Poorly resolved multiplet from 2.5–3.5 ppm, nonsymmetric. The subsequent 200 MHz spectrum of this sample is even more poorly resolved suggesting it is picking up water of hydration.

The mass spectrum shows the parent ion at m/e 216 and major fragment ions at m/e 197, 174, 160, 145, 131, 85, 56, and 42.

IR(KBr, hydrate): 3.0(b), 3.45, 5.96(w), 6.74, 6.81, 7.49, 7.98, 8.41, 8.65, 8.93, 9.05, 9.35(b), 9.61, 9.82, 10.3, 10.83, 11.7(b), 13.07 and 13.22 μ.

EXAMPLE 12 (E5985-116,117,132,134,136)

17-Oxo-1,5,9,13-tetraaza-17-phosphatricyclo[7.7.1.0$^{5,17}$.0$^{13,17}$]heptadecane was prepared as follows

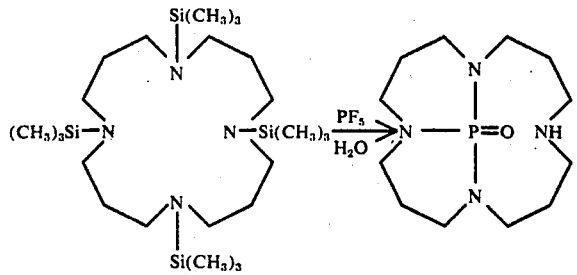

1,5,9,13-Tetrakis(trimethylsilyl)-1,5,9,13-tetraazacyclohexadecane was prepared from the corresponding amine essentially by the procedure of Example 1A, bp 159°–161° at 0.1 mm pressure. Then 9.9 g of this material and 60 ml of dry chlorobenzene were frozen in a 500-ml flask, evacuated, and pressured with 475 ml of pentafluorophosphorane gas. This mixture was stirred at −20°, pressured to 1 atmosphere with nitrogen gas (400 ml), and warmed to 20°. After 30 min, an nmr sample indicated that the formation of fluorotrimethylsilane was about 50% complete. The mixture was refluxed for 30 min without any apparent change in the nmr spectrum (except removal of gaseous fluorotrimethylsilane). Refluxing was continued in two portions for an additional 26.5 hr. The nmr spectrum now indicated that about three-fourths of the original silyl groups had been displaced. After standing 3 months, 37% of the clear solution was decanted from a gummy residue, and concentrated to 2.5 g using a hot water bath at 0.1 mm. This residue was distilled bulb-to-bulb at 0.1 mm pressure. All isolated fractions contained an average of less than one silyl group per four nitrogens. At 190°–200° oven temperature (0.1 mm) some crystalline solid sublimed followed by yellow oil which distilled at 210° and 0.1 mm pressure. Some crystals of the solid (mp 115°–127°) were scraped from the receiver and were identified as the above phosphine oxide by nmr and mass spectroscopy.

NMR(CDCl$_3$): two groups of complex multiplets at 4.0–2.5 and 2.2–1.2 ppm in the ratio 2:1.2 (theoretical ratio 2:1).

NMR($^{19}$F, CDCl$_3$ + F-11): no absorptions.

The mass spectrum shows the parent ion of the above phosphine oxide at m/e 272 with no ions at m/e 274 or 255 expected for the non-hydrolyzed product $C_{12}H_{24}N_4PF$.

The ir spectrum of this solid in chloroform solution shows NH or water bands and prominent bands at 7.4, 7.9, 8.4, 8.7 and 8.9 μ and a series of five bands of about equal intensity from 9.2 to 10 μ.

EXAMPLE 13 (E8186-13,35)

11-Oxo-1,4,7-triaza-11-phosphatricyclo[5.3.1.0$^{4,1-1}$]undecane was prepared as follows

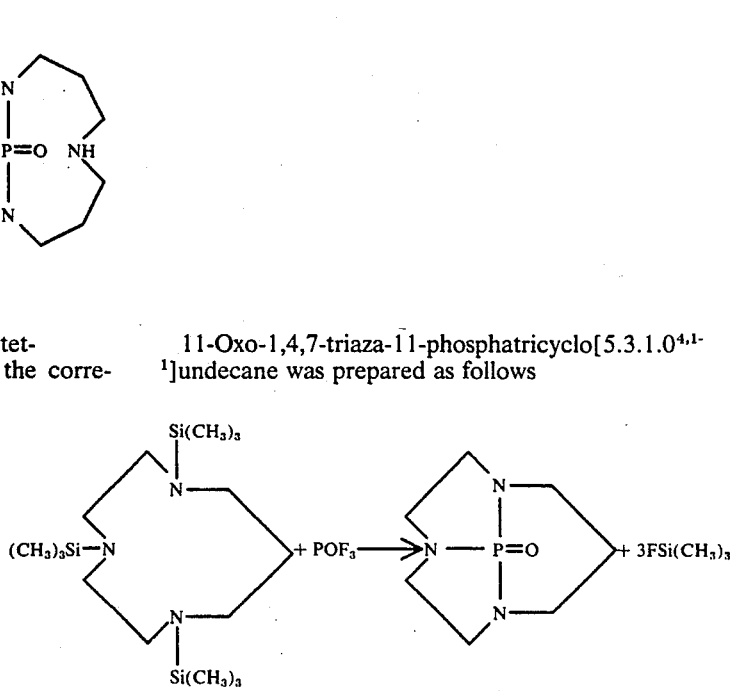

1,4,7-Tris(trimethylsilyl)-1,4,7-triazacyclodecane was prepared essentially by the procedure of Example 1A from 1,4,7-triazacyclodecane. In a 20 ml flask 0.29 g of the silylated starting material (distilled bulb-to-bulb at 105°/0.1 mm) and 1 ml of chlorobenzene was frozen, evacuated and pressured with 20 ml of phosphorus oxyfluoride gas. This mixture was heated at 100° in a closed system for 13 hr, concentrated, and then distilled bulb-to-bulb at 115°–130° oven temperature and 0.02 mm pressure to give 100 mg (66% yield) of semi-crystalline distillate which was used for ir, nmr, and mass spectra, which identify the above product as a major component.

NMR(CDCl$_3$): δ 4.2–2.6 (complex multiplet) and 2.5–0.6 broad multiplet.

The mass spectrum shows the parent ion at m/e 187 and major fragment ions at m/e 159, 149, 148, 147, 145, 131, 111, 90, 84, 77, 75, 73, 70, 66, 59, 56, 54, 49, 47, 45, 44, 43, 42, 41, 29, 27, 26, 18, and 16.

EXAMPLE 14 (E8186-65,66)

13-oxo-1,4,7-triaza-13-phosphatricyclo[5.5.1.0$^{4,13}$]-tridecane was prepared as follows

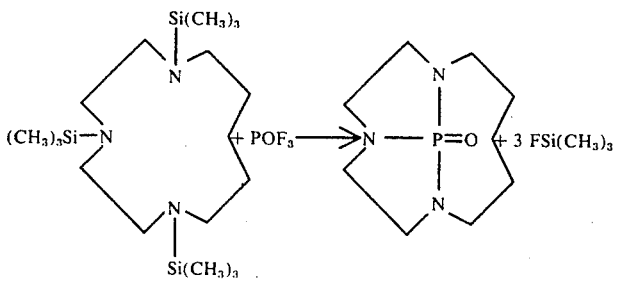

1,4,7-Tris(trimethylsilyl)-1,4,7-triazacyclododecane was prepared from 1,4,7-triazacyclododecane trishydrochloride with six equivalents of n-butyllithium essentially by the procedure of Example 1 (A). In a 50 ml flask a solution of 0.675 g of the tris silyl compound (distilled bulb-to-bulb at 95°–125°/0.1 mm) in 2.5 ml of chlorobenzene was frozen, evacuated, and pressured with 40 ml of phosphorus oxyfluoride gas. The flask was sealed and the mixture heated overnight at 100°. Then the mixture was refluxed under a nitrogen atmosphere for 4 hours. A sample indicated (by nmr) that two-thirds of the silyl groups had reacted. Refluxing was continued for 5.8 hours under a nitrogen pressure of 960–1040 mm of mercury. A sample at this time showed almost complete displacement of the silyl groups as fluorotrimethylsilane. The mixture remaining (about 80–85% of the original) was concentrated under vacuum and distilled bulb-to-bulb under vacuum (0.1 mm). The fraction collected at 80°–100° oven temperature consisted of solidified condensate in the mouth of the receiver, mp 78°–86.5°. This sample (~30 mg) was used for ir and mass spectroscopy which identify this material as 13-oxo-1,4,7-triaza-13-phosphatricyclo[5.5.1.0$^{4,13}$]-tridecane. It was recrystallized in part from cyclohexane giving needles, mp 86°–87.5°.

IR (Nujol): 7.42, 7.54, 7.66, 7.8, 8.2 (st), 8.52 (st), 8.68, 8.77, 9.0, 9.08, 9.44, 9.68, 10.10, 10.25, 10.68, 11.34, 11.53, 11.73, 12.41, 13.42, 13.77 (st) and 14.10 (st).

The mass spectrum shows a strong parent ion at m/e 215 and major fragment ions at m/e 173, 160, 159, 131, 84, 56, 55, 47, 44, 42, 41, 30, 29, 27 and 15.

EXAMPLE 15 (E5985-62,63 and E8186-68)

The following examples show the flame retardant properties of the products of this invention.

A. In 1.75 ml vials 100-mg samples of the products of Examples 1B (13-fluoro-1,4,7,10-tetraaza-13-phosphatetracyclo[5.5.1.0$^{4,13}$.0$^{10,13}$]tridecane) and 4 (13-phenyl-1,4,7,10-tetraaza-13-phosphatetracyclo[5.5.1.0$^{4,13}$.0$^{10,13}$]tridecane) were dissolved in 1.0 g of dimethylformamide. Heating was necessary in the case of the product of Example 4. Samples (0.5 g) of 100% cotton cloth (Sears Supima) cut in strips (~0.75 × 4 inches) were soaked for 1 hour in each of these vials and in a vial containing only the solvent. After drying 20 hours in the air, these strips were vertically suspended and lighted at the bottom with a match.

The blank sample completely burned in 20–25 sec. The flame rapidly climbed and the ash was a white powder after total consumption of the glowing residue.

In the case of the products of Examples 1B and 4 the cloth was totaly inflamed in 30 sec. Progress of the flame climbing was clearly slower than for the blank and there was considerable smoking. The ash was a black carbonaceous residue which did not glow.

Similarly samples of the products of Examples 1B and 4 (0.02 g each) were dissolved in 1.0 g of acetone and soaked into cotton strips. After 1 hour of drying, these strips were similarly tested along with a blank. The burning rate was similar (15 sec) in all three samples. However, in the samples containing the products of Examples 1B and 4 the ash did not glow and left a black carbon residue. The blank was totally consumed leaving a white ash.

B. In 1.75 ml vials 60 mg samples of the products of Examples 6 (13-(1-pyrrolidyl)-1,4,7,10-tetraaza-13-phosphatetracyclo[5.5.1.0$^{4,13}$.0$^{10,13}$]tridecane) and 14 (13-oxo-1,4,7-triaza-13-phosphatricyclo[5.5.1.0$^{4,13}$]-tridecane) were dissolved in 0.5 ml of dimethylformamide, heating was necessary in the case of the product of Example 6. Samples (0.18 g) of 100% cotton cloth (Sears Supima) cut in strips (~1 × 10 cm) were soaked in each vial and in a vial containing 0.5 ml of dimethylformamide only (blank). The vial were heated in a bath at 100° for 1 min and then allowed to sit for 6.5 hours at 25°. The treated strips were dried for 8.5 hr in air and then 2 hours at 50–70° under a nitrogen sweep at partial vacuum. The strips were vertically suspended and lighted at the bottom with a match.

The blank sample supported a flame which totally enflamed the sample in 18 seconds and left a grey ash after total consumption of the glowing residue.

The strips soaked with the products of Examples 6 and 14 did not spontaneously burn after lighting. Exposure to the match flame for 15 seconds did char the cloth with considerable smoking, but it immediately self-extinguished leaving a black carbonaceous residue which did not glow.

I claim:

1. A tetracyclic tetraamino phosphorane of the formula

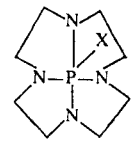

wherein X is F, $C_6H_5$, R, OR, $NR_2$ or $N\overparen{(CH_2)_{2-6}}$, where R is $C_1$–$C_6$ alkyl, and the monomethyl iodide salts thereof.

2. The tetracyclic tetraamino phosphorane of claim 1 in which X is F.

3. The tetracyclic tetraamino phosphorane of claim 1 in which X = $OCH_3$.

4. The tetracyclic tetraamino phosphorane of claim 1 in which X = $C_4H_9$.

5. The tetracyclic tetraamino phosphorane of claim 1 in which X = $CH_3$.

6. The tetracyclic tetraamino phosphorane of claim 1 in which X = $C_6H_5$.

7. The method of preparing a tetracyclic tetraamino phosphorane which comprises reacting a silylated cyclic tetraamine of the formula

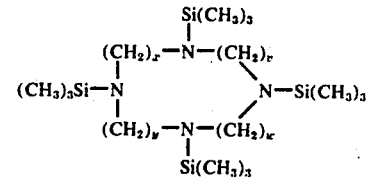

wherein $x$, $y$, $v$ and $w$ are each 2 or 3 with a fluorophosphorane selected from the group consisting of $XPF_4$ and $POF_3$ wherein X is F, $C_6H_5$, or $C_1$–$C_6$ alkyl at a temperature from room temperature to 200° C.

8. The method of claim 7 in which the fluorophosphorane is $XPF_4$.

9. The method of claim 1 in which the fluorophosphorane is $POF_3$.

* * * * *